United States Patent [19]

Freed et al.

[11] Patent Number: 4,540,806

[45] Date of Patent: Sep. 10, 1985

[54] BENZOCYCLOALKANE AMINES

[75] Inventors: Meier E. Freed, Paoli, Pa.; Magid A. Abou-Gharbia, Wilmington, Del.

[73] Assignee: American Home Products Corporation, New York, N.Y.

[21] Appl. No.: 564,588

[22] Filed: Dec. 22, 1983

[51] Int. Cl.³ ............... C07C 87/02; C07C 101/72; C07C 103/127; A61K 31/22
[52] U.S. Cl. .................. 560/139; 564/222; 564/300; 564/427; 514/816
[58] Field of Search ............... 560/139; 564/222, 300, 564/427

[56] References Cited

U.S. PATENT DOCUMENTS

| | | | |
|---|---|---|---|
| 3,836,670 | 9/1974 | Freed et al. | 564/427 X |
| 4,034,041 | 7/1977 | Freed et al. | 564/427 |
| 4,049,701 | 9/1977 | Freed et al. | 560/130 |
| 4,076,953 | 2/1978 | Freed et al. | 560/142 |
| 4,156,694 | 5/1979 | Hewett et al. | 564/222 X |
| 4,299,984 | 11/1981 | Hewett et al. | 564/222 X |

OTHER PUBLICATIONS

*Tetrahedron*, vol. 24, No. 12, 1968, pp. 4605–4623, Kitahonoki et al.
Weast, R. C., ed., *CRC Handbook of Chemistry and Physics*, 60th Ed., 1979, pp. C-13, C-16.
Fieser and Fieser, *Organic Chemistry*, 3rd. Ed., 1956, p. 179.
Derwent: 58866V.
Derwent: 69477X.
Derwent: 27960W.
Derwent: 05449X.
Derwent: 26119X.
Derwent: 41892X.
Derwent: 68628X.
Derwent: 68630X.
Derwent: 72072X.
Derwent: 93052X.
Derwent: 05492Y.
Derwent: 40396Y.

*Primary Examiner*—Natalie Trousof
*Assistant Examiner*—Patricia M. Scott
*Attorney, Agent, or Firm*—Richard K. Jackson

[57] ABSTRACT

Benzocycloalkane amine derivatives and their non-toxic acid addition salts as novel analgesic agents.

9 Claims, No Drawings

BENZOCYCLOALKANE AMINES

BACKGROUND OF THE INVENTION

Benzocycloalkane amines are known analgesic agents as exemplified in U.S. Pat. Nos. 4,034,041; 4,049,701 and 4,076,953.

DESCRIPTION OF THE INVENTION

In accordance with this invention there is provided a group of novel, substituted benzocycloalkane amines possessing analgesic activity and the following structural formula:

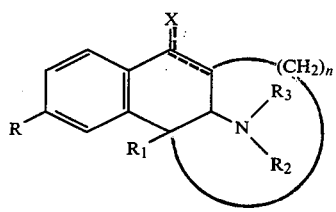

in which

R is hydrogen, alkyl of 1 to 6 carbon atoms, alkoxy of 1 to 6 carbon atoms, hydroxy, alkanoyloxy of 2 to 6 carbon atoms, aralkoxy of 7 to 12 carbon atoms, halo or trifluoromethyl;

$R_1$ is alkyl of 1 to 6 carbon atoms, alkenyl of 2 to 6 carbon atoms or phenylalkyl of 7 to 12 carbon atoms;

$R_2$ is hydrogen, alkyl of 1 to 6 carbon atoms or phenylalkyl of 7 to 12 carbon atoms;

$R_3$ is hydrogen, alkyl of 1 to 6 carbon atoms, alkoxy of 1 to 6 carbon atoms, hydroxy, phenylalkyl of 7 to 12 carbon atoms or alkanoyl of 2 to 6 carbon atoms;

X is hydrogen, oxygen or hydroxy;

n is one of the integers 2, 3, 4, 5 or 6;

the dotted lines represent unsaturation between the cycloalkyl ring and X when X is oxygen and within the cycloalkyl ring when X is hydrogen;

or a pharmaceutically acceptable salt thereof.

The preferred ketone analgesic agents of this invention present the following structural formula:

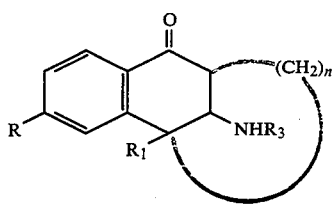

in which

R is hydroxy, alkanoyloxy of 2 to 4 carbon atoms, alkoxy of 1 to 4 carbon atoms, phenylalkoxy of 7 to 9 carbon atoms;

$R_1$ is alkyl of 1 to 3 carbon atoms;

$R_3$ is hydrogen, alkyl of 1 to 3 carbon atoms, phenylalkyl of 7 to 9 carbon atoms or alkanoyl of 2 to 4 carbon atoms;

n is one of the integers 4 or 5;

or a pharmaceutically acceptable salt thereof.

The preferred hydroxy substituted analgesic agent of the invention presents the following structural formula:

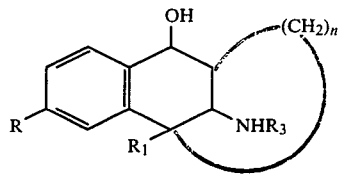

in which

R is hydroxy, alkanoyloxy of 2 to 4 carbon atoms, alkoxy of 1 to 4 carbon atoms, phenylalkoxy of 7 to 9 carbon atoms;

$R_1$ is alkyl of 1 to 3 carbon atoms;

$R_3$ is hydrogen, alkyl of 1 to 3 carbon atoms, phenylalkyl of 7 to 9 carbon atoms or alkanoyl of 2 to 4 carbon atoms;

n is one of the integers 4 or 5;

or a pharmaceutically acceptable salt thereof.

The preferred cycloalkene analgesic agent of this invention presents the following structural formula:

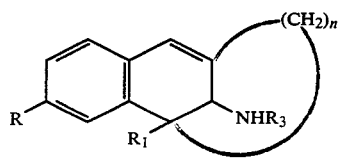

in which

R is hydroxy, alkanoyloxy of 2 to 4 carbon atoms, alkoxy of 1 to 4 carbon atoms, phenylalkoxy of 7 to 9 carbon atoms;

$R_1$ is alkyl of 1 to 3 carbon atoms;

$R_3$ is hydrogen, alkyl of 1 to 3 carbon atoms, phenylalkyl of 7 to 9 carbon atoms or alkanoyl of 2 to 4 carbon atoms;

n is one of the integers 4 or 5;

or a pharmaceutically acceptable salt thereof.

The pharmaceutically acceptable salts of the compounds of this invention are produced conventionally by neutralization of the free base or by metathetical displacement with either organic or inorganic acids such as hydrochloric, hydrobromic, phosphoric, sulfuric, sulfonic, nitric, methylsulfonic, acetic, maleic, succinic, fumaric, tartaric, citric, salicylic, lactic, naphthalenesulfonic acid, and the like. The halo substituents preferred in the compounds depicted, supra, are chlorine, bromine or fluorine.

The compounds of this invention are prepared by the following procedure, which representatively illustrates the production of a product which is representative of the other compounds of the invention:

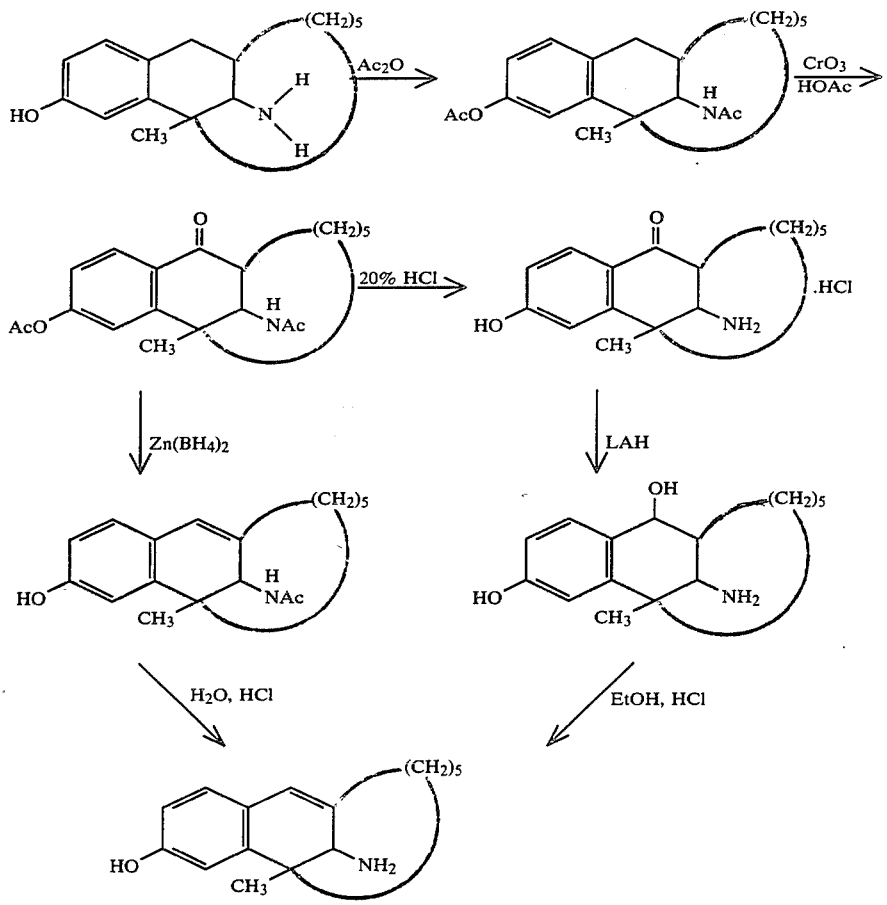

The analgesic activity of the compounds of this invention was established following the standard test procedure of D'Amour and Smith, *Journal of Pharmacology*, 72, 74 (1941), wherein the compounds were administered intraperitoneally to rats, and the time required for response to a pain stimulus caused by a high intensity beam of light shining on the tail measured. The compounds of this invention disclosed in Examples 3, 4 and 5, infra, representative of the other compounds disclosed and claimed, demonstrated analgesic activity in response to the standard test procedure in two out of six animals at 25 mg/kg with the products of Examples 3 and 4 demonstrating a response in five out of six upon subcutaneous administration of 2.5 mg/kg.

Thus, compounds of this invention may be employed as analgesic agents in warm-blooded animals, e.g., mice, rats, rabbits, monkeys and so forth, alone or in combination with pharmacologically acceptable carriers.

The dosage employed upon administration will vary with the form of administration and the compound chosen. Furthermore, it will vary with the particular subject under treatment. Generally treatment is initiated with small dosages substantially less than the optimum dose. Thereafter, the dose is increased in small increments until the optimum effect under the circumstances is reached. In general, the compounds of the invention are not desirably administered at a concentration level that will generally afford effective results without causing any harmful or deleterious side effects.

The following examples illustrate the best mode contemplated by the inventors for the practice of their invention.

EXAMPLE 1

13-Acetylamino-5,6,7,8,9,10,11,12-octahydro-5-methyl-5,11-methanobenzocyclodecen-3-hydroxyacetate To a solution of 2.45 g (0.01 mole) of 13-amino-5,6,7,8,9,10,11,12-octahydro-5-methyl-5,11-methanobenzocyclodecen-3-ol in 20 mL of dry pyridine was added 4 g. (0.04 mole) of acetic anhydride while maintaining the temperature at 25° C. The reaction mixture was stirred overnight and the solvent was evaporated under reduced pressure. The residue was dissolved in diethyl ether and washed with dilute hydrochloric acid solution and water. Evaporation of the ether layer afforded an oily product which was crystallized from diethyl ether-pentane (1:1) to afford 2.1 g. (65.6% yield) of the title compound, mp 115°–116° C., $[\alpha]_D^{25}$ −44.42 (c 0.95% $CH_3OH$).

Analysis for: $C_{20}H_{27}NO_3$; Calculated: C, 72.92; H, 8.26; N, 4.25; Found: C, 72.75; H, 8.21; N, 4.13.

EXAMPLE 2

13-Acetylamino-6,7,8,9,10,11-hexahydro-3-acetyloxy-5-methyl-5,11-methanobenzocyclodecen-12(5H)-one To a stirred solution of 4 g. (0.012 mole) of 13-acetylamino-5,6,7,8,9,10,11,12-octahydro-5-methyl-5,11-methanobenzocyclodecen-3-hydroxyacetate in 800 mL of glacial acetic acid was added 35 mL of glacial acetic acid containing 3 g. (0.032 mole) of chromic trioxide and 1.5 mL of water. The reaction mixture was stirred at room temperature overnight and excess $CrO_3$ was then decomposed by adding 25 mL of isopropanol. The solvent was removed under reduced pressure and the residue was extracted with methylene chloride. The methylene chloride layer was washed with dilute sodium hydrogen carbonate and water and was concentrated under reduced pressure. The residue was chromatographed on silica gel using ethyl acetate as eluent. This afforded 1.1 g. (25% yield) of the title compound, mp 133°–137° C.

Analysis for: $C_{20}H_{26}NO_4$; Calculated: C, 66.46; H, 7.53; N, 3.88; Found: C, 66.78; H, 7.56; N, 3.80.

EXAMPLE 3

13-Amino-6,7,8,9,10,11-hexahydro-3-hydroxy-5-methyl-5,11-methanobenzocyclodecen-12(5H)-one 13-Acetylamino-6,7,8,9,10,11-hexahydro-3-acetoxy-5-methyl-5,11-methanobenzocyclodecen-12(5H)-one (3 g., 0.008 mole) was refluxed with 10 mL of 20% hydrochloric acid in the presence of a few drops of ethanol for 24 hours. The reaction mixture was boiled with 0.5 g. of charcoal, filtered and the solvent was evaporated under reduced pressure. The remaining solid was recrystallized from acetone-ethanol (5:1) to afford 1.5 g. (65% yield) of the title compound as a hydrochloride dihydrate, mp 256°–258° C.

Analysis for: $C_{16}H_{21}NO_2 \cdot HCl \cdot 2H_2O$; Calculated: C, 57.91; H, 7.59; N, 4.22; Found: C, 57.29; H, 7.22; N, 3.97.

EXAMPLE 4

13-Amino-5,6,7,8,9,10,11,12-octahydro-5-methyl-5,11-methanobenzocyclodecen-3,12-diol To a stirred suspension 2 g. of lithium aluminum hydride (LAH) in 250 mL of tetrahydrofuran (THF) was added a slurry of 1 g. (0.003 mole) of 13-amino-6,7,8,9,10,11-hexahydro-3-hydroxy-5-methyl-5,11-methanobenzocyclodecen-12(5H)-one hydrochloride dihydrate in 50 mL of THF over a period of 1 hour. The reaction mixture was refluxed for 25 hours and then cooled and excess LAH was decomposed by careful addition of 2 mL of water. The reaction mixture was filtered and the filtrate washed with aqueous ammonium chloride, dried (anhydrous $Na_2SO_4$) and evaporated under reduced pressure to afford a white residue which was recrystallized from acetone-ethanol (5:1) to afford 500 mg (68% yield) of the title compound, mp 232°–235° C.

Analysis for: $C_{16}H_{23}NO_2$; Calculated: C, 73.56; H, 8.81; N, 5.36; Found: C, 73.08; H, 8.90; N, 4.81.

EXAMPLE 5

13-Amino-5,6,7,8,9,10-hexahydro-5-methyl-5,11-methanobenzocyclodecen-3-ol hydrochloride hemihydrate 13-Amino-5,6,7,8,9,10,11,12-octahydro-5-methyl-5,11-methanobenzocyclodecen-3,12-diol (0.7 g., 0.002 mole) was dissolved in 20 mL of boiling ethanol. To this solution was added 5 mL ethanol saturated with hydrogen chloride and was allowed to stand overnight. The solvent was evaporated under reduced pressure and the resulting residue was recrystallized from acetone-ethanol (5:1) to afford 400 mg (70% yield) of the title compound as a hydrochloride hemihydrate, mp 216°–218° C.

Analysis for: $C_{16}H_{21}NO \cdot HCl \cdot \frac{1}{2}H_2O$; Calculated: C, 66.55; H, 7.97; N, 4.85; Found: C, 66.45; H, 7.81; N, 4.57.

EXAMPLE 6

13-Acetylamino-5,6,7,8,9,10-hexahydro-5-methyl-5,11-methanobenzocyclodecen-3-ol

Zinc chloride (5 g., 0.03 mole) was dissolved in 60 mL of diethyl ether and the insoluble material was filtered. The ethereal solution was added dropwise to sodium borohydride (3.5 g., 0.009 mole) in 150 mL of ether. The reaction mixture was stirred overnight at room temperature. The separated solid was allowed to settle and the supernatent liquid was removed by decantation. This ethereal solution of zinc borohydride was added to a solution of 4 g. (0.01 mole) of 13-acetylamino-6,7,8,9,10,11-hexahydro-3-acetyloxy-5-methyl-5,11-methanobenzocyclodecen-12(5H)-one in 50 mL of diethyl ether and the reaction mixture was stirred at room temperature for 48 hours. Excess zinc borohydride was decomposed by adding 3 mL of glacial acetic acid in 15 mL of water. The reaction mixture was filtered and the layer was washed with water, dried (anhydrous $Na_2SO_4$) and evaporated under reduced pressure. The separated solid was slurried in methanol and was heated while adding a few drops of dilute hydrochloric acid. The solvent was evaporated under vacuo and the solid was chromatographed on silica gel using ethyl acetate as eluent which afforded 2.3 g. (80.9% yield) of the title compound, mp 246°–249° C.

Analysis for: $C_{18}H_{22}NO_2$; Calculated: C, 76.08; H, 7.79; N, 4.92; Found: C, 76.05; H, 7.93; N, 4.95.

What is claimed is:

1. A compound of the formula

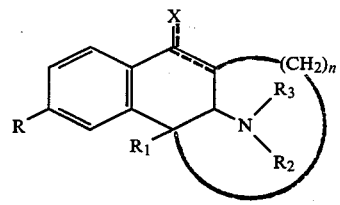

in which

R is alkoxy of 1 to 6 carbon atoms, hydroxy, alkanoyloxy of 2 to 6 carbon atoms, aralkoxy of 7 to 12 carbon atoms;

$R_1$ is alkyl of 1 to 6 carbon atoms, alkenyl of 2 to 6 carbon atoms, or phenylalkyl of 7 to 12 carbon atoms;

$R_2$ is hydrogen, alkyl of 1 to 6 carbon atoms or phenylalkyl of 7 to 12 carbon atoms;

$R_3$ is hydrogen, alkyl of 1 to 6 carbon atoms, alkoxy of 1 to 6 carbon atoms, hydroxy, phenylalkyl of 7 to 12 carbon atoms or alkanoyl of 2 to 6 carbon atoms;

X is hydrogen, oxygen or hydroxy;

n is one of the integers 2, 3, 4, 5 or 6;

the dotted lines represent unsaturation between the cycloalkyl ring and X when X is oxygen and within the cycloalkyl ring when X is hydrogen;

or a pharmaceutically acceptable salt thereof.

2. A compound of claim 1 of the formula:

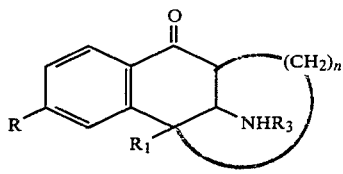

in which
R is hydroxy, alkanoyloxy of 2 to 4 carbon atoms, alkoxy of 1 to 4 carbon atoms, phenylalkoxy of 7 to 9 carbon atoms;
$R_1$ is alkyl of 1 to 3 carbon atoms;
$R_3$ is hydrogen, alkyl of 1 to 3 carbon atoms, phenylalkyl of 7 to 9 carbon atoms or alkanoyl of 2 to 4 carbon atoms;
n is one of the integers 4 or 5;
or a pharmaceutically acceptable salt thereof.

3. A compound of claim 1 of the formula:

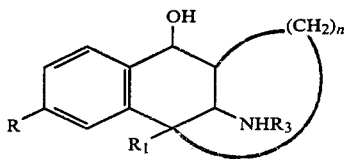

in which
R is hydroxy, alkanoyloxy of 2 to 4 carbon atoms, alkoxy of 1 to 4 carbon atoms, phenylalkoxy of 7 to 9 carbon atoms;
$R_1$ is alkyl of 1 to 3 carbon atoms;
$R_3$ is hydrogen, alkyl of 1 to 3 carbon atoms, phenylalkyl of 7 to 9 carbon atoms or alkanoyl of 2 to 4 carbon atoms;
n is one of the integers 4 or 5;
or a pharmaceutically acceptable salt thereof.

4. A compound of claim 1 of the formula:

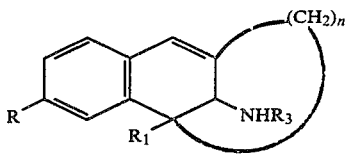

in which
R is hydroxy, alkanoyloxy of 2 to 4 carbon atoms, alkoxy of 1 to 4 carbon atoms, phenylalkoxy of 7 to 9 carbon atoms;
$R_1$ is alkyl of 1 to 3 carbon atoms;
$R_3$ is hydrogen, alkyl of 1 to 3 carbon atoms, phenylalkyl of 7 to 9 carbon atoms or alkanoyl of 2 to 4 carbon atoms;
n is one of the integers 4 or 5;
or a pharmaceutically acceptable salt thereof.

5. A compound of claim 2 which is 13-acetylamino-6,7,8,9,10,11-hexahydro-3-acetyloxy-5-methyl-5,11-methanobenzocyclodecen-12(5H)-one.

6. A compound of claim 2 which is 13-amino-6,7,8,9,10,11-hexahydro-3-hydroxy-5-methyl-5,11-methanobenzocyclodecen-12(5H)-one.

7. A compound of claim 3 which is 13-amino-5,6,7,8,9,10,11,12-octahydro-5-methyl-5,11-methanobenzocyclodecen-3,12-diol.

8. A compound of claim 4 which is 13-amino-5,6,7,8,9,10-hexahydro-5-methyl-5,11-methanobenzocyclodecen-3-ol.

9. A compound of claim 4 which is 13-acetylamino-5,6,7,8,9,10-hexahydro-5-methyl-5,11-methanobenzocyclodecen-3-ol.

* * * * *